(12) United States Patent
Cross et al.

(10) Patent No.: US 11,291,758 B2
(45) Date of Patent: Apr. 5, 2022

(54) COLLECTION SYSTEM FOR MANAGING OUTFLOW FROM A SURGICAL PROCEDURE

(71) Applicant: Covidien LP, Mansfield, MA (US)

(72) Inventors: Damian J. Cross, Woburn, MA (US); Jordan Whisler, Brookline, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/985,631

(22) Filed: Aug. 5, 2020

(65) Prior Publication Data

US 2022/0040387 A1 Feb. 10, 2022

(51) Int. Cl.
*A61M 1/00* (2006.01)
*A61B 46/23* (2016.01)
*A61B 46/00* (2016.01)

(52) U.S. Cl.
CPC ............. *A61M 1/802* (2021.05); *A61B 46/23* (2016.02); *A61B 46/30* (2016.02); *A61M 1/732* (2021.05); *A61M 1/743* (2021.05); *A61B 2046/236* (2016.02); *A61M 2205/583* (2013.01)

(58) Field of Classification Search
CPC ...... A61M 1/802; A61M 1/732; A61M 1/743; A61M 2205/58; A61B 46/23; A61B 46/30; A61B 2046/236
See application file for complete search history.

(56) References Cited

U.S. PATENT DOCUMENTS

| 5,265,638 | A | 11/1993 | Fischer et al. |
| 5,460,490 | A | 10/1995 | Carr et al. |
| 6,224,617 | B1 | 5/2001 | Saadat et al. |
| 6,626,827 | B1 | 9/2003 | Felix et al. |
| 7,597,662 | B2 | 10/2009 | Litscher et al. |
| 9,943,639 | B2 | 4/2018 | Germain et al. |
| 2011/0060300 | A1* | 3/2011 | Weig ..................... A61M 1/743 604/319 |
| 2017/0143880 | A1* | 5/2017 | Luxon ..................... A61M 1/83 |
| 2017/0172796 | A1 | 6/2017 | Biancalana et al. |

OTHER PUBLICATIONS

Extended European Search Report dated Dec. 8, 2021 issued in corresponding EP Appln. No. 21189446.4.

* cited by examiner

*Primary Examiner* — Tatyana Zalukaeva
*Assistant Examiner* — Hans Kaliher
(74) *Attorney, Agent, or Firm* — Carter, DeLuca & Farrell LLP

(57) ABSTRACT

A fluid collection system includes a vacuum source, a collection vessel, and a surgical drape. A fluid outflow line is connected between the surgical drape and the collection vessel. The fluid outflow line provides a path for fluid to the collection vessel. A suction line is connected with the collection vessel. The suction line provides suction to draw fluid through the fluid outflow line to the collection vessel. The suction line branches into a first suction line and a second suction line parallel with the first suction line. The first suction line and the second suction line are each connected with the vacuum source. A flow restrictor is disposed along the first suction line. A valve is disposed along the second suction line. The valve is opened in a pulsatile fashion when fluid is present in the surgical drape to increase a level of suction provided to the surgical drape.

20 Claims, 3 Drawing Sheets

COLLECTION SYSTEM FOR MANAGING OUTFLOW FROM A SURGICAL PROCEDURE

FIELD

The disclosure relates generally to surgical systems and, more particularly, to a collection system for managing outflow from a gynecological surgical procedure.

BACKGROUND

Surgical procedures, such as tissue resection procedures, may be performed endoscopically within an organ, such as a uterus, by inserting an endoscope into the uterus and passing a tissue resection device through the endoscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

In accordance with aspects of the disclosure, a collection system for managing outflow from a gynecological surgical procedure includes a surgical instrument, a vacuum source, a first collection vessel, and a first fluid outflow line connected between the surgical instrument and the first collection vessel. The first fluid outflow line provides an outflow path for fluid from the surgical instrument to the first collection vessel. A first suction line is connected between the vacuum source and the first collection vessel. The first suction line provides suction to draw fluid from the surgical instrument to the first collection vessel. A surgical drape is positioned to collect liquid. A second fluid outflow line is connected between the surgical drape and a second collection vessel. The second fluid outflow line provides an outflow path for fluid from the surgical drape to the second collection vessel. A second suction line is connected with the second collection vessel. The second suction line provides suction to draw fluid from the surgical drape to the second collection vessel. A portion of the second suction line branches between a third suction line and a fourth suction line arranged in-parallel with the third suction line. The third suction line and the fourth suction line are each connected with the vacuum source. A flow restrictor is disposed along the third suction line. A valve is disposed along the fourth suction line. The valve is opened in a pulsatile fashion when fluid is present in the surgical drape to increase a level of suction provided to the surgical drape.

In some aspects of the disclosure, a sensor is connected with the third suction line and the valve. The sensor detects a presence of fluid in the surgical drape. The sensor opens the valve in the pulsatile fashion to suction fluid from the surgical drape to the second collection vessel. The sensor detects the presence of fluid in the surgical drape based on an increase in vacuum pressure in the third suction line.

In some aspects of the disclosure, opening or closing of the valve maintains at least some suction at the surgical instrument when fluid is present in the surgical drape. The valve remains closed when fluid is absent from the surgical drape.

In some aspects of the disclosure, the first suction line is coupled to the second suction line.

In some aspects of the disclosure, the amount of suction provided to the surgical drape when fluid is present in the surgical drape is less than a maximum suction level that can be provided by the vacuum source.

In some aspects of the disclosure, a first end of the second fluid outflow line is connected with a bottom of the surgical drape, and a second end of the second fluid outflow line is connected with a top of the second collection vessel. The second fluid outflow line suctions fluid against a force of gravity from the surgical drape to the second collection vessel.

In some aspects of the disclosure, an operating console operates the vacuum source. The operating console includes a display device.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
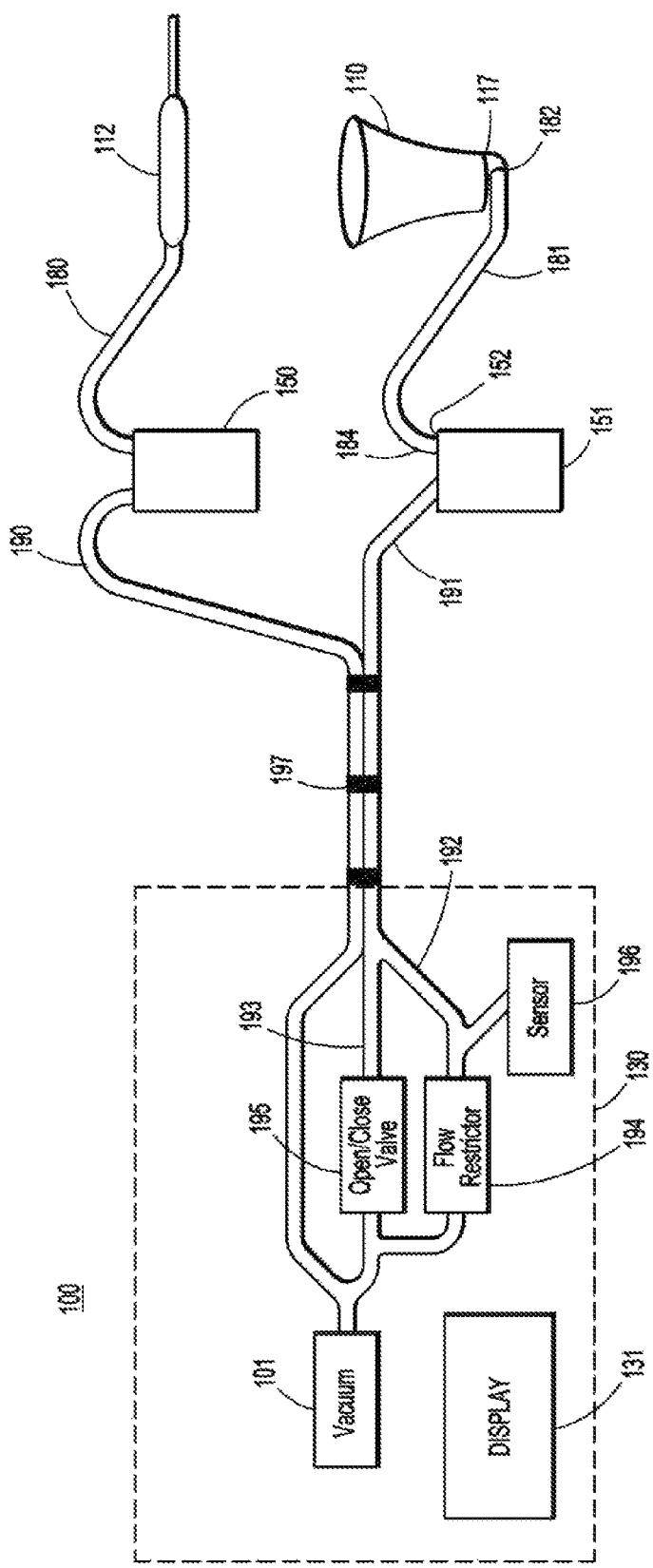
FIG. 1 illustrates a collection system for managing outflow from a gynecological surgical procedure for use in accordance with the aspects and features of the disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

The term "about" as used herein may be inclusive of the stated value and means within an acceptable range of variation for the particular value as determined by one of ordinary skill in the art, considering tolerances (e.g., material, manufacturing, use, environmental, etc.) as well as the measurement in question and the error associated with measurement of the particular quantity (e.g., the limitations of the measurement system). For example, "about:" may mean within one or more standard deviations of the stated value.

Descriptions of technical features or aspects of an exemplary configuration of the disclosure should typically be considered as available and applicable to other similar features or aspects in another exemplary configuration of the disclosure. Accordingly, technical features described herein according to one exemplary configuration of the disclosure may be applicable to other exemplary configurations of the disclosure, and thus duplicative descriptions may be omitted herein.

Exemplary configurations of the disclosure will be described more fully below (e.g., with reference to the accompanying drawings). Like reference numerals may refer to like elements throughout the specification and drawings.

Referring to FIG. 1 a surgical system provided in accordance with aspects of the disclosure is shown generally identified by reference numeral 100. Surgical system 100 may include surgical system 200 described in more detail below with reference to FIG. 2 and surgical system 300 described in more detail below with reference to FIG. 3. Surgical system 100 may include each of the surgical systems 200 and 300 that are each connected with a common control console 130 and a common vacuum source 101. However, each of surgical systems 200 and 300 may operate as standalone systems.

The surgical system 100 is a collection system that may be employed for managing outflow from a gynecological surgical procedure. Surgical system 100 includes a surgical instrument 112 (e.g., a handpiece for gynecological procedures such as a hysteroscope, tissue resection instrument, etc.), a vacuum source 101, a first collection vessel 150, and a first fluid outflow line 180 connected between the surgical instrument 112 and the first collection vessel 150. The first fluid outflow line 180 provides an outflow path for fluid from the surgical instrument 112 to the first collection vessel 150. A first suction line 190 is connected between the vacuum source 101 and the first collection vessel 150. The first suction line 190 provides suction to draw fluid from the surgical instrument 112 to the first collection vessel 150. A surgical drape 110 is positioned to collect liquid. A second fluid outflow line 181 is connected between the surgical drape 110 and a second collection vessel 151. The second fluid outflow line 181 provides an outflow path for fluid from the surgical drape 110 to the second collection vessel 151. A second suction line 191 is connected with the second collection vessel 151. The second suction line 191 provides suction to draw fluid from the surgical drape 110 to the second collection vessel 151. The second suction line 191 branches between a third suction line 192 and a fourth suction line 193 arranged in-parallel with the third suction line 192. The third suction line 192 and the fourth suction line 193 are each connected with the vacuum source 101. A flow restrictor 194 is disposed along the third suction line 192. A valve 195 is disposed along the fourth suction line 193.

The valve 195 is opened, e.g., in a pulsatile fashion, when fluid is present in the surgical drape 110 to increase a level of suction provided to the surgical drape 110. The open valve 195 has less resistance than flow restrictor 194, and thus a majority of the suction may be provided through the open valve 195. The valve 195 remains in a closed configuration when fluid is not present in the surgical drape 110.

A first end 182 of the second fluid outflow line 181 is connected with a bottom 117 of the surgical drape 110. A second end 184 of the second fluid outflow line 181 is connected with a top 152 of the second collection vessel 151. The second fluid outflow line 181 provides a path for fluid to be suctioned from the surgical drape 110 to the second collection vessel 151. Thus, fluid may be suctioned against a force of gravity away from the surgical drape 110 without an appreciable time delay.

In a conventional system, suctioning fluid against the force of gravity may increase the amount of time for fluid evacuation from a surgical drape because the vacuum pressure must increase enough to suction fluid a vertical height equal to the height of the collection vessel. The time elapsed while the vacuum pressure increases may leave fluid in the surgical drape for a sufficient period of time that a user may believe the system is not operating correctly.

An operating console 130 operates the vacuum source 101. The operating console 130 includes a display device 131, such as a digital touch screen display. The valve 195, flow restrictor 194, sensor 196, vacuum source 101, and portions of the suction lines 190, 191, 192 and/or 193 can be located in the operating console 130, or each of these components can be separate from the operating console 130.

A sensor 196 is connected with the third suction line 192 and the valve 195. The sensor 196 detects a presence of fluid in the surgical drape 110 based on an increase in vacuum pressure in the second suction line 192. The sensor 196 detects the presence of fluid in the surgical drape 110 when suction builds up within the second suction line 192 since the second suction line 192 is not longer open to atmosphere.

The first suction line 190 may be at least partially coupled to the second suction line 191. For example, at least one elastomeric band 197 or other suitable mechanical, e.g., clip, tie, etc., may secure the first suction line 190 to the second suction line 191.

In use, the vacuum source 101 is configured to simultaneously provide suction to each of the surgical instrument 112 and the surgical drape 110. However, the surgical drape 110 is generally open to atmosphere and an amount of suction provided to the surgical instrument 112 is generally not equal to the amount of suction provided to surgical drape 110. Generally, when fluid is present at the surgical drape 110 an amount of suction provided to the surgical drape 110 increases to draw the fluid from the surgical drape 110 to the second collection vessel 151.

As an example, a maximum amount of suction that can be provided by the vacuum source 101 may be about 300 mmHG, which is distributed between the surgical instrument 112 and the surgical drape 110. When fluid is not present in the surgical drape 110, about 200 mmHG of suction is provided to the surgical instrument 112, while about 100 mmHG of suction is provided to the surgical drape 110 via third suction line 192. In this circumstance, the valve 195 remains closed and suction is not provided through fourth suction line 193. However, when fluid is present in the surgical drape 110, the valve 195 may be triggered to open and thus suction is provided through third suction line 192 and fourth suction line 193 in-parallel. Thus, when fluid is present in the surgical drape 110, the distribution of suction is changed such that about 200 mmHG of suction is provided to the surgical drape 110, while about 100 mmHG of suction is provided to the surgical instrument 112. In this arrangement, some level of suction is always provided to each of the surgical drape 110 and the surgical instrument 112. When fluid is present in the surgical drape 110, the valve 195 is moved from a closed position to an open position, e.g., in a pulsatile fashion, such that the flow through fourth suction line 193 is "throttled" (i.e., repeatedly pulsed from a closed position to an open position) such that suction is simultaneously provided through each of suction lines 192 and 193. Throttling the flow through the fourth suction line 193 increases the suction provided to the surgical drape (e.g., from about 100 mmHG to about 200 mmHG) while partially and temporarily reducing suction at the surgical instrument 112 (e.g., from about 200 mmHG to about 100 mmHG). This allows fluid to be drawn out of the surgical drape 110 to the second collection vessel 151 at an increased rate, while maintaining a sufficient level of suction at the surgical instrument 112.

Figure 2:
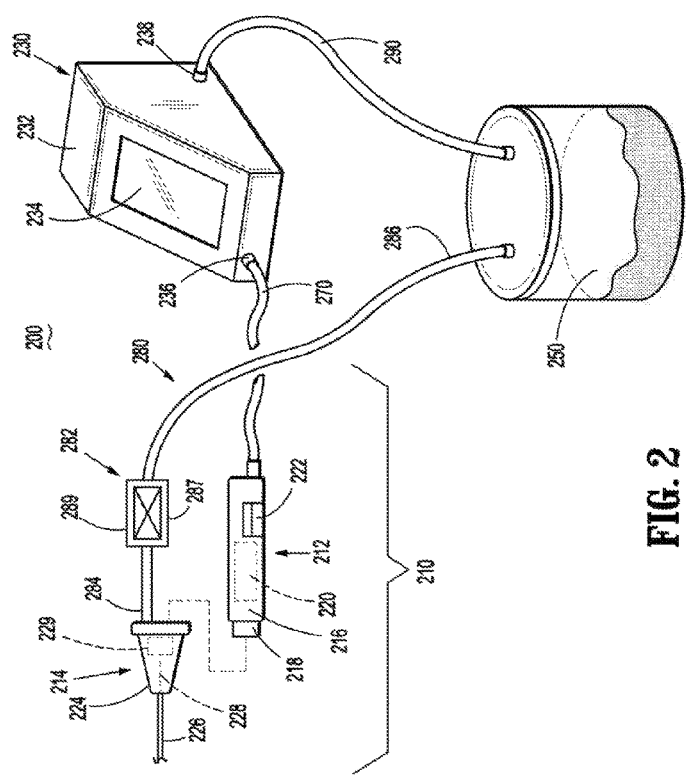
FIG. 2 is a perspective view of a first portion of the collection system of FIG. 1.

Referring to FIG. 2 a surgical system provided in accordance with aspects of the disclosure is shown generally identified by reference numeral 200. Surgical system 200 generally includes a surgical instrument 210, a control console 230, and a collection vessel 250. Surgical system 200 further includes a cable 270, outflow tubing 280, and vacuum tubing 290.

Surgical instrument 210 includes a surgical instrument such as tissue resecting handpiece 212 that may be configured as a reusable component and a tissue resecting end effector assembly 214 that may be configured as a single-use, disposable component. Handpiece 212 includes a housing 216 to facilitate grasping and manipulation of surgical instrument 210 by a user. Handpiece 212 further includes an output interface 218 configured to operably engage end effector assembly 214, a motor 220 disposed within housing 216 and operably coupled to output interface 218 to drive output interface 218 and, thus, drive end effector assembly 214, and a module dock 222 configured to mechanically engage and electrically coupled to a valve module 282 associated with outflow tubing 280, as detailed below. Cable 270 electrically couples handpiece 212 and control console 230 with one another and, more specifically, electrically couples control console 230 with motor 220 to power and control operation of motor 220 and electrically couples control console 230 with valve module 282 to enable communication of, for example, identification, setting, and control information therebetween. In aspects of the disclosure, cable 270 is fixedly attached to handpiece 212 and releasably couplable with control console 230, although other configurations are also contemplated.

End effector assembly 214 includes a proximal hub 224 configured to releasably engage housing 216 of handpiece 212 to releasably mechanically engage end effector assembly 214 with handpiece 212. End effector assembly 214 further includes an outer shaft 226 extending distally from proximal hub 224 and a cutting shaft 228 extending through outer shaft 226. A proximal end of cutting shaft 228 extends into proximal hub 224 wherein an input interface 229 is engaged with cutting shaft 228. Input interface 229 is configured to operably couple to output interface 218 of handpiece 212 when proximal hub 224 is engaged with housing 216 such that, when motor 220 is activated to drive output interface 218, input interface 229 is driven in a corresponding manner to thereby move cutting shaft 228 within and relative to outer shaft 226.

Outer shaft 226, as noted above, extends distally from proximal hub 224 and, in aspects of the disclosure, is stationary relative to proximal hub 224, although other configurations are also contemplated. Outer shaft 226 may define a window (not shown) through a side wall thereof towards a distal end thereof to provide access to cutting shaft 228 which is rotatably and/or translatably disposed within outer shaft 226. Cutting shaft 228 may define an opening (not shown) towards the distal end thereof providing access to the interior thereof and may include a serrated cutting edge (not shown) surrounding the opening, although other suitable cutting-edge configurations are also contemplated. Alternatively, or additionally, outer shaft 226 may include a cutting edge defined about the window thereof.

Motor 220, as noted above, is activated to move cutting shaft 228 and, more specifically, to drive rotation and/or translation of cutting shaft 228 relative to outer shaft 226. Control console 230, coupled to motor 220 via cable 270, enables selective powering and controlling of motor 220 and, thus, selective rotation and/or translation of cutting shaft 228 relative to outer shaft 226 to resect tissue adjacent the distal end of end effector assembly 214.

Continuing with reference to FIG. 2, a distal end 284 of outflow tubing 280 is coupled to proximal hub 224 of end effector assembly 214 in fluid communication with the interior of cutting shaft 228 and/or the interior of outer shaft 226 such that fluid, tissue, and debris drawn into cutting shaft 228 and/or outer shaft 226 may be suctioned, under vacuum, through end effector assembly 214 and outflow tubing 280. A proximal end 286 of outflow tubing 280 is coupled to collection canister 250 to enable the fluid, tissue, and debris suctioned through end effector assembly 214 and outflow tubing 280 to be deposited within collection canister 250. Distal end 284 of outflow tubing 280 may be fixedly secured to proximal hub 224 while proximal end 286 of outflow tubing 280 is configured to releasably couple to collection canister 250, although other configurations are also contemplated.

Outflow tubing 280 further includes, as noted above, a valve module 282. Valve module 282 is disposed between distal and proximal ends 284, 286, respectively, of outflow tubing 280. Valve module 282 includes a controllable valve 287 disposed within the flow path defined through outflow tubing 280 to selectively permit and inhibit flow therethrough and/or to control the flow rate therethrough, and a communication device 289, e.g., a RFID tag, storing information regarding end effector assembly 214 such as, for example, identifying information, use setting information, etc. Valve module 282 is configured for releasable engagement with module dock 222 of handpiece in electrical communication therewith. With valve module 282 engaged with module dock 222 and, as detailed above, module dock 222 coupled to control console 230 via cable 270, the information stored on communication device 289 of valve module 282 may be communicated to control console 230 (via a communication receiver, e.g., an RFID reader, of module dock 222 and cable 270) for use in controlling motor 220 to drive end effector assembly 214 in accordance with the settings, parameters, and/or other configuration thereof, and/or to control controllable valve 287, e.g., in accordance with the activation/deactivation of motor 220, the position and/or orientation of cutting shaft 228, or in any other suitable manner. Thus, end effector assemblies 214 of various different configurations (different length, diameter, cutting arrangement, outflow tube configuration, etc.) may be utilized with handpiece 212 and control console 230 in a plug-and-play manner.

Referring still to FIG. 2, collection canister 250, as noted above, is coupled to proximal end 286 of outflow tubing 280 to receive the fluid, tissue, and debris suctioned through end effector assembly 214 and outflow tubing 280. Vacuum tubing 290 is coupled between collection canister 250 and a vacuum source (see, e.g., vacuum source 101 of FIG. 1) disposed within or otherwise associated with control console 230 such that, upon activation of the vacuum source, negative pressure is established through collection canister 250, outflow tubing 280, and the interior of cutting shaft 228 and/or outer shaft 226 of end effector assembly 214 to draw the fluids, tissue, and debris into and through cutting shaft 228 and/or outer shaft 226, outflow tubing 280, and into collection canister 250.

Control console 230, as noted above, is configured to receive information from communication device 289 of valve module 282 and, based at least in part on that information, control motor 220 of handpiece 212, control controllable valve 287 of valve module 282, and operate the vacuum source thereof to resect tissue and suction resected tissue, fluid, and debris through end effector assembly 214 and outflow tubing 280 for depositing into collection canister 250. Control console 230 generally includes an outer housing 232, a touch-screen display 234 accessible from the exterior of outer housing 232, a cable port 236 configured to receive cable 270, and a vacuum tube port 238 configured to receive vacuum tube 290. Outer housing 232 houses internal electronics (not shown) as well as the vacuum source.

Control console 230 may be configured to connect to a mains power supply (not shown) for powering control console 230. Further, control console 230 may be configured to receive user input, e.g., use information, setting selections, etc., via touch-screen display 234 or a peripheral input device (not shown) coupled to control console 230. Operational input, e.g., ON/OFF signals, power level settings (HI power vs. LO power), etc., may likewise be input via touch-screen display 234 or a peripheral input device (not shown) such as, for example, a footswitch (not shown), a handswitch (not shown) disposed on handpiece 212, etc.

In preparation for use, end effector assembly 214 is engaged with handpiece 212, valve module 282 is engaged within module dock 222, cable 270 is coupled to control console 230 (and handpiece 212 if not already connected thereto), proximal end 286 of outflow tubing 280 is coupled to collection canister 250 (and distal end 284 thereof to end effector assembly 214 if not already connected thereto), and vacuum tubing 290 is coupled between vacuum tube input 238 of control console 230 and collection canister 250. The connections between valve module 282 and module dock 222 and between cable 270 and control console 2, as detailed above, enable communication of information regarding end effector assembly 214 (and, in embodiments, outflow tubing 280) to control console 230 to enable control console 230 to adjust setting information, use parameters, etc., based thereupon.

In use, upon an activation input provided to control console 230, control console 230 powers and controls motor 220 of handpiece 212 to, in turn, drive cutting shaft 228 of end effector assembly 214 to resect tissue adjacent the distal end of end effector assembly 214. During activation, control console 230 also controls controllable valve 287 and the vacuum source disposed within control console 230 to suction fluid, the resected tissue, and debris through cutting shaft 228 and/or outer shaft 226, outflow tubing 280, and into collection canister 250.

As demonstrated above, surgical system 200 provides a configuration whereby handpiece 212 and control console 230 remain isolated from the fluid, tissue, and debris suctioned through surgical instrument 210 and into collection canister 250, thus facilitating the cleaning process for reuse of handpiece 212 and control console 230. More specifically, while valve module 282 is coupled to module dock 222, module dock 222 communicates signals (electrical and/or mechanical) to control controllable valve 287 of valve module 282 without requiring contact with the flow path through outflow tubing 280 and/or controllable valve 287. End effector assembly 214 and outflow tubing 280, on the other hand, may together be configured as a single-use component that is discarded after use.

Figure 3:
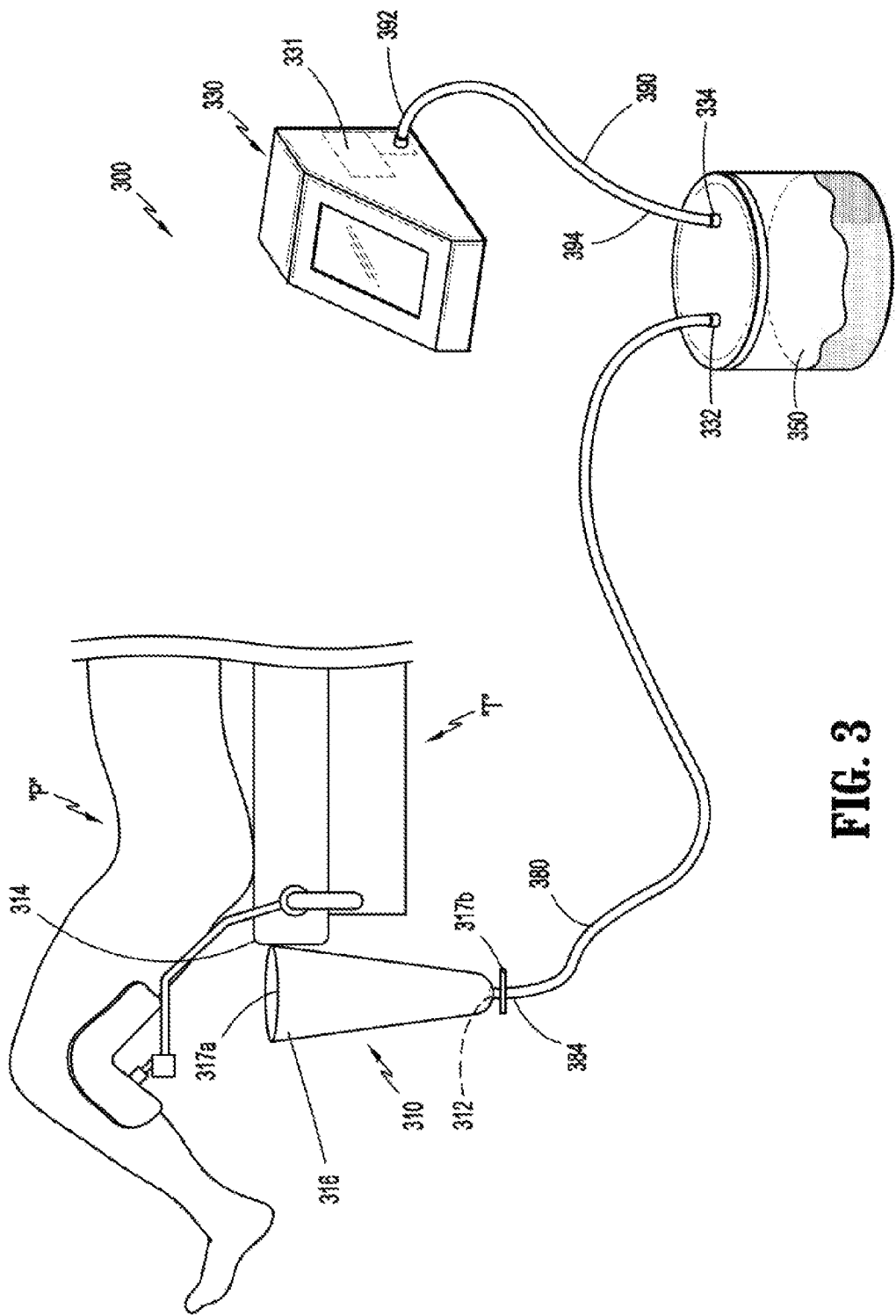
FIG. 3 is a perspective view of a second portion of the collection system of FIG. 1.

Referring to FIG. 3, an outflow collection system provided in accordance with aspects of the disclosure is shown generally identified by reference numeral 300. Outflow collection system 300 includes a surgical drape 310, a fluid outflow line 320, a collection vessel 350, a suction line 390, and a vacuum source, e.g., a control console 330 including a vacuum pump 331. Outflow collection system 300 may further include one or more instrument lines (not shown) connected between one or more surgical instruments (not shown), e.g., an hysteroscope, a tissue resection device, etc., and the collection vessel 350 or an additional collection vessel.

Continuing with reference to FIG. 3, surgical drape 310 is positioned with a flap 314 thereof positioned underneath a patient "P," e.g., between the patient "P" and the operating table "T," with a funnel-shaped body 316 of the surgical drape 310 depending from the flap 314 and an end of the operating table "T." The funnel-shaped body 316 defines an open, upper base end 317a configured to collect liquid, e.g., dripping out of the patient "P" and/or onto the operating table "T," and a lower, apex end 317b that defines outflow opening 312, through which the collected liquid is configured to flow. The distal end 384 of suction line 380 is connected to outflow opening 312.

Suction line 380 extends to collection vessel 350 and is connected to a first port 332 of collection vessel 350. Collection vessel 350 further includes a second port 334 configured to receive distal end 394 end of suction line 390. The proximal end 392 of suction line 390 is coupled to a vacuum source, e.g., vacuum pump 331 of control console 330, such that, upon activation of vacuum pump 331, negative pressure is established through collection vessel 350 and fluid outflow line 380 to draw liquids collected in surgical drape 310 from surgical drape 310, through fluid outflow line 380, to collection vessel 350.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A collection system for managing outflow from a gynecological surgical procedure, the collection system comprising:
   a surgical instrument;
   a vacuum source;
   a first collection vessel;
   a first fluid outflow line connected between the surgical instrument and the first collection vessel, the first fluid outflow line configured to provide an outflow path for fluid from the surgical instrument to the first collection vessel;
   a first suction line connected between the vacuum source and the first collection vessel, the first suction line configured to provide suction to draw fluid from the surgical instrument to the first collection vessel;
   a surgical drape configured to collect liquid;
   a second collection vessel;
   a second fluid outflow line connected between the surgical drape and the second collection vessel, the second fluid outflow line configured to provide an outflow path for fluid from the surgical drape to the second collection vessel;

a second suction line connected with the second collection vessel, the second suction line configured to provide suction to draw fluid from the surgical drape to the second collection vessel, wherein a portion of the second suction line branches between a third suction line and a fourth suction line arranged in-parallel with the third suction line, the third suction line and the fourth suction line each connected with the vacuum source;

a flow restrictor disposed along the third suction line;

a control console; and a valve disposed along the fourth suction line, wherein the valve is configured to be automatically opened by the control console in a pulsatile fashion when fluid is present in the surgical drape to increase a level of suction provided to the surgical drape.

2. The collection system of claim 1, further including a sensor connected with the third suction line and the valve, the sensor configured to detect a presence of fluid in the surgical drape, and the sensor configured to open the valve in the pulsatile fashion to suction fluid from the surgical drape to the second collection vessel.

3. The collection system of claim 2, wherein the sensor detects the presence of fluid in the surgical drape based on an increase in vacuum pressure in the third suction line.

4. The collection system of claim 1, wherein opening or closing of the valve is configured to maintain at least some suction at the surgical instrument when fluid is present in the surgical drape.

5. The collection system of claim 1, wherein the valve remains closed when fluid is absent from the surgical drape.

6. The collection system of claim 1, wherein the first suction line is coupled to the second suction line.

7. The collection system of claim 1, wherein the amount of suction provided to the surgical drape when fluid is present in the surgical drape is less than a maximum suction level that can be provided by the vacuum source.

8. The collection system of claim 1, wherein a first end of the second fluid outflow line is connected with a bottom of the surgical drape, and a second end of the second fluid outflow line is connected with a top of the second collection vessel.

9. The collection system of claim 8, wherein the second fluid outflow line is configured to suction fluid against a force of gravity from the surgical drape to the second collection vessel.

10. The collection system of claim 1, further including an operating console configured to operate the vacuum source.

11. The collection system of claim 10, wherein the operating console includes a display device.

12. A collection system for managing outflow from a gynecological surgical procedure, the collection system comprising:
a vacuum source;
a collection vessel;
a surgical drape configured to collect liquid;
a fluid outflow line connected between the surgical drape and the collection vessel, the fluid outflow line configured to provide an outflow path for fluid to the collection vessel;
a suction line connected with the collection vessel, the suction line configured to provide suction to draw fluid through the fluid outflow line to the collection vessel, wherein the suction line branches into a first suction line and a second suction line arranged in-parallel with the first suction line, the first suction line and the second suction line each connected with the vacuum source;
a flow restrictor disposed along the third suction line;
a control console; and
a valve disposed along the fourth suction line, wherein the valve is configured to be automatically opened by the control console in a pulsatile fashion when fluid is present in the surgical drape to increase a level of suction provided to the surgical drape.

13. The collection system of claim 12, further including a sensor connected with the first suction line and the valve, the sensor configured to detect a presence of fluid in the surgical drape, and the sensor configured to open the valve in the pulsatile fashion to suction fluid from the surgical drape to the collection vessel.

14. The collection system of claim 13, wherein the sensor detects the presence of fluid in the surgical drape based on an increase in vacuum pressure in the third suction line.

15. The collection system of claim 12, wherein the valve remains closed when fluid is absent from the surgical drape.

16. The collection system of claim 12, wherein the amount of suction provided to the surgical drape when fluid is present in the surgical drape is less than a maximum suction level that can be provided by the vacuum source.

17. The collection system of claim 12, wherein a first end of the fluid outflow line is connected with a bottom of the surgical drape, and a second end of the fluid outflow line is connected with a top of the second collection vessel.

18. The collection system of claim 17, wherein the fluid outflow line is configured to suction fluid against a force of gravity from the surgical drape to the collection vessel.

19. The collection system of claim 12, further including an operating console configured to operate the vacuum source.

20. The collection system of claim 19, wherein the operating console includes a display device.

* * * * *